United States Patent
Tanaka et al.

(10) Patent No.: US 9,918,963 B2
(45) Date of Patent: *Mar. 20, 2018

(54) THERAPEUTIC AGENT FOR DISEASE BASED ON INHIBITORY EFFECT OF MACROPHAGE MIGRATION INHIBITORY FACTOR

(71) Applicant: TOYAMA CHEMICAL CO., LTD., Shinjuku-ku (JP)

(72) Inventors: Keiichi Tanaka, Toyama (JP); Kimiko Morimoto, Toyama (JP)

(73) Assignee: TOYAMA CHEMICAL CO., LTD., Shinjuku-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/132,892

(22) Filed: Apr. 19, 2016

(65) Prior Publication Data

US 2016/0228404 A1 Aug. 11, 2016

Related U.S. Application Data

(63) Continuation of application No. 14/647,931, filed as application No. PCT/JP2014/069026 on Jul. 17, 2014, now abandoned.

(30) Foreign Application Priority Data

Jul. 18, 2013 (JP) .................................. 2013-149690

(51) Int. Cl.
*A61K 31/352* (2006.01)
*C07D 311/30* (2006.01)
*C07D 311/24* (2006.01)
*C07D 311/22* (2006.01)

(52) U.S. Cl.
CPC .......... *A61K 31/352* (2013.01); *C07D 311/22* (2013.01); *C07D 311/24* (2013.01); *C07D 311/30* (2013.01)

(58) Field of Classification Search
CPC ...... A61K 31/352; C07D 31/30; C07D 31/24; C07D 31/22
See application file for complete search history.

(56) References Cited

U.S. PATENT DOCUMENTS

| | | | |
|---|---|---|---|
| 4,954,518 A | 9/1990 | Takano et al. | |
| 5,922,755 A * | 7/1999 | Tanaka | C07D 311/22 514/210.11 |
| 6,166,068 A | 12/2000 | Tanaka et al. | |
| 2015/0080356 A1 | 3/2015 | Tanaka | |

FOREIGN PATENT DOCUMENTS

| | | |
|---|---|---|
| DE | 38 34 204 A1 | 4/1989 |
| EP | 0 695 547 A1 | 2/1996 |
| JP | 2-49778 A | 2/1990 |
| WO | 94/23714 A1 | 10/1994 |
| WO | WO 2006/108671 A1 | 10/2006 |
| WO | WO 2007/042035 A2 | 4/2007 |

OTHER PUBLICATIONS

Types-MS, 2017, http://www.nationalmssociety.org/What-is-MS/Types-of-MS.*
EAE, 2017, https://en.wikipedia.org/wiki/Experimental_autoimmune_encephalomyelitis.*
PRMS, 2017, http://www.webmd.com/multiple-sclerosis/guide/progressive-relapsing-multiple-sclerosis#1.*
Aikawa et al., 1998, caplus an 1998:497653.*
Denic et al., Pathophysiology, 2011, 18(1), 12 pages.*
Combined Taiwanese Office Action and Search Report dated Dec. 14, 2016 in patent application No. 103124716 with English translation of categories of cited documents.
Richard E. Jones, et al. "Myelin basic protein-specific T lymphocytes induce chronic relapsing experimental autoimmune encephalomyelitis in lymphocyte-deficient (SCID) mice", Journal of Neuroimmunology, vol. 93, 1999, pp. 92-101.
Extended European Search Report dated Jun. 29, 2016 in Patent Application No. 16169414.6.
Fang Du, et al., "T-614, a novel immunomodulator, attenuates joint inflammation and articular damage in collagen-induced arthritis" Arthritis Research & Therapy, Available online: http://arthritis-research.com/content/10/6/R136, vol. 10, No. 6, XP021046839, Nov. 19, 2008, 11 Pages.
Tanaka et al.—"Pharmacological Studies on 3-Formylamino-7-methylsulfonylamino-6-phenoxy-4H-1-benzopyran-4-one (T-614), a Novel Antiinflammatory Agent. 3$^{rd}$ Communication: The Involvement of Bradykinin in Its Analgesic Actions", J. Pharmacobio-Dyn., vol. 15, No. 11, pp. 641-647 (1992).
Kam et al.—"Synthesis and bradykinin inhibitory activity of novel non-peptide compounds, and evaluation of in vivo analgesic activity", Bioorganic & Medicinal Chemistry vol. 18, No. 6, 2010, pp. 2327-2336.

(Continued)

*Primary Examiner* — Sun Jae Yoo
(74) *Attorney, Agent, or Firm* — Oblon, McClelland, Maier & Neustadt, L.L.P.

(57) ABSTRACT

A method for treating the relapsing-remitting or secondary progressive multiple sclerosis at the time of relapse, by administering a benzopyran derivative of the following formula or a salt thereof,

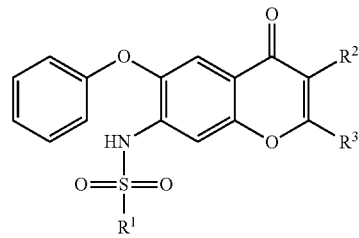

where $R^1$ represents an optionally substituted $C_{1-6}$ alkyl group, one of $R^2$ and $R^3$ represents a hydrogen atom, and the other of $R^2$ and $R^3$ represents a hydrogen atom, an optionally substituted amino group, an optionally substituted acylamino group, an optionally substituted carbamoyl group or an optionally substituted aryl group.

6 Claims, 1 Drawing Sheet

(56) References Cited

OTHER PUBLICATIONS

Woolf et al.—"Neuropathic pain: aetiology, symptoms, mechanisms, and management", The Lancet, vol. 353, Jun. 5, 1999, pp. 1959-1964.

Noseworthy et al.—"Multiple Sclerosis" Review Article, The New England Journal of Medicine, vol. 343, No. 13, pp. 938-952, Sep. 28, 2000.

Morand et al.—"MIF: a new cytokine link between rheumatoid arthritis and atherosclerosis", Nature Reviews Drug Discovery, vol. 5, Apr. 13, 2006, pp. 399-410.

Rosengren et al.—"The Immunoregulatory Mediator Macrophage Migration Inhibitory Factor (MIF) Catalyzes a Tautomerization Reaction", Molecular Medicine, vol. 2, No. 1, Jan. 1996, pp. 143-149.

Alexander et al.—"Macrophage migration inhibitory factor (MIF) is essential for inflammatory and neuropathic pain and enhances pain in response to stress", Experimental Neurology, vol. 236 (2012), pp. 351-362.

Wang et al.—"Spinal Macrophage Migration Inhibitory Factor is a Major Contributor to Rodent Neuropathic Pain-like Hypersensitivity", Anesthesiology, vol. 114, No. 3, pp. 643-659, Mar. 2011.

Niino et al.—"Macrophage migration inhibitory factor in the cerebrospinal fluid of patients with conventional and optic-spinal forms of multiple sclerosis and neuro-Behçet's disease", Journal of the Neurological Sciences vol. 179 (2000), pp. 127-131.

Powell et al.—"Cutting Edge: Macrophage Migration Inhibitory Factor is Necessary for Progression of Experimental Autoimmune Encephalomyelitis", The Journal of Immunology, 2005, vol. 175, pp. 5611-5614.

Mangano et al.—"Variable effects of cyclophosphamide in rodent models of experimental allergic encephalomyelitis", British Society for Immunology, Clinical and Experimental Immunology, vol. 159, pp. 159-168.

Leone et al.—"An Assessment of the Mechanistic Differences Between Two Integrin $\alpha_4\beta_1$ Inhibitors, the Monoclonal Antibody TA-2 and the Small Molecule BIO5192, in Rat Experimental Autoimmune Encephalomyelitis", The Journal of Pharmacology and Experimental Therapeutics, vol. 305, 2003, pp. 1150-1162.

Theien et al.—"Discordant effects of anti-VLA-4 treatment before and after onset of relapsing experimental autoimmune encephalomyelitis", The Journal of Clinical Investigation, Apr. 2001, vol. 107, No. 8, pp. 995-1006.

Inaba et al.—"Synthesis and Antiiflammatory Activity of 7-Methanesulfonylamino-6-phenoxychromones. Antiarthritic Effect of the 3-Formylamino Compound (T-614) in Chronic Inflammatory Disease Models", Chem. Pharm. Bull. vol. 48, No. 1, pp. 131-139 (2000).

Tanaka et al.—"Pharmacological Studies on 3-Formylamino-7-methylsulfonylamino-6-phenoxy-4H-1-benzopyran-4-one (T-614), a Novel Antiinflammatory Agent, $4^{th}$ Communication: Inhibitory Effect on the Production of Interleukin-1 and Interleukin-6", J. Pharmacobio-Dyn., vol. 15, pp. 649-655 (1992).

Tanaka et al.—"Pharmacological Studies on T-614, a Novel Antiinflammatory Agent: Effect on Type II Collagen-Induced Arthritis in DBA/1J Mice and Spontaneous Arthritis in MRL/I Mice", Int. J. Immunotherapy, vol. 9, pp. 69-78(1993).

Aikawa et al.—"A new anti-rheumatic drug, T-614, effectively suppresses the development of autoimmune encephalomyelitis", Journal of Neuroimmunology vol. 89(1998), pp. 35-42.

Aikawa et al.—"Inhibitory action of an anti-rheumatic drug, T-614, to rat experimental autoimmune encephalomyelitis", Proceedings of the Japanese Society for Immunology, vol. 25, 1995, p. 315.

Warabi—"Role of IL-1 and potential therapies in multiple sclerosis", Drug Discovery Today: Therapeutic Strategies, vol. 4, No. 1, 2007, pp. 19-24.

Takano et al., 1989, caplus an 1989:614389.

* cited by examiner

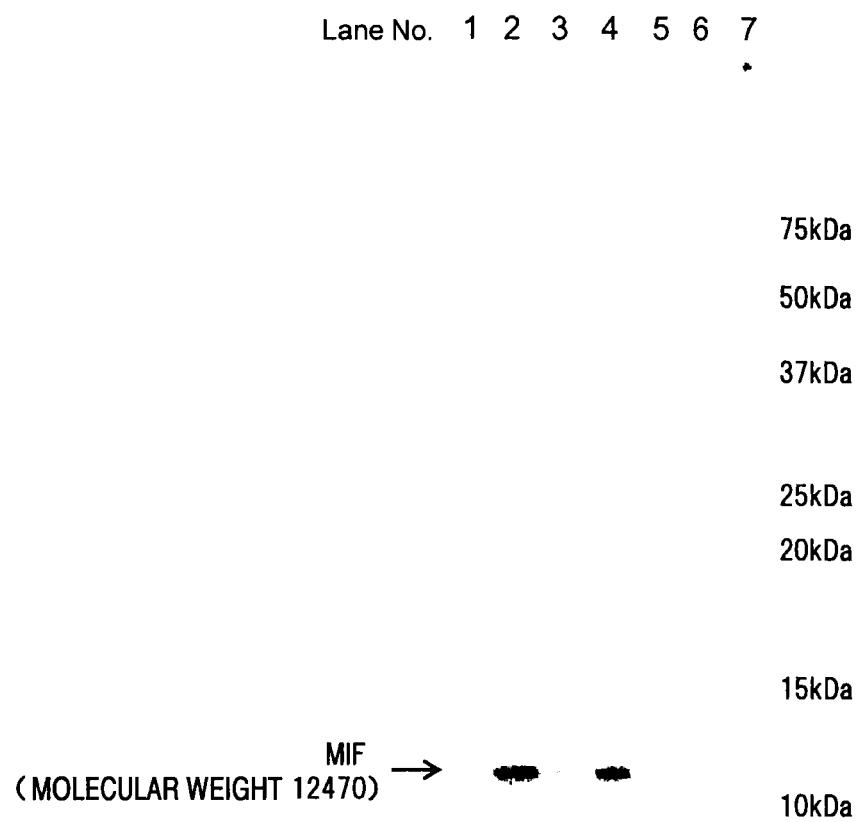

THERAPEUTIC AGENT FOR DISEASE BASED ON INHIBITORY EFFECT OF MACROPHAGE MIGRATION INHIBITORY FACTOR

CROSS REFERENCE TO RELATED APPLICATION(S)

This application is a continuation of U.S. application Ser. No. 14/647,931, filed on May 28, 2015, which is a national stage patent application of international patent application PCT/JP14/69026, filed on Jul. 17, 2014, the text of which is incorporated by reference, and claims foreign priority to JP 2013-149690, filed on Jul. 18, 2013, the entire content of which is incorporated herein by reference.

TECHNICAL FIELD

The present invention relates to a method of using a benzopyran derivative having macrophage migration inhibitory factor (hereinafter referred to as MIF) inhibitory activity or a salt thereof for a therapeutic or preventive treatment of a nervous system disease such as neuropathic pain or multiple sclerosis. Furthermore, it relates to a pharmaceutical composition containing a benzopyran derivative or a salt thereof useful for a therapeutic or preventive treatment of a nervous system disease.

BACKGROUND ART

Neuropathic pain (hereinafter referred to as NP) is a kind of chronic pain diseases caused by peripheral nerve and/or central nerve disorder and functional disorder due to cancer or physical injury. Such a pain has lost its original significance of alerting tissue disorder but is no more than a pain. The quality of life (QOL) of a patient is remarkably reduced due to such a pain.

The symptom of NP is, in addition to continuous spontaneous pain, mainly allodynia that a tactile stimulus is felt as a drastic pain. Such a pain is strongly resistant to non-steroidal anti-inflammatory drugs (hereinafter referred to as NSAIDs) such as ibuprofen, and is resistant also to morphine, that is, a narcotic analgesic (Non Patent Document 1).

The pathologic physiology and the cause of NP have not been completely elucidated yet, but the followings have been proved as a result of recent fundamental research:

(1) NP is induced by a damage of peripheral and/or central nerve.

(2) A variety of cytokines and chemokines are released from damaged nerve cells.

(3) The released cytokines and the like cause remarkable activation of microglia known as an immunocompetent cell for the central nerve system.

NP is treated for purposes of relieving the pain, increasing the functional capacity of the patient, and improving his/her activity. For these purposes, for example, administration of an antidepressant, a narcotic analgesic or the like, a nerve block treatment, and an acupuncture and moxibustion treatment are performed. However, any excellent therapeutic method based on the developing mechanism of NP has not been known, and an excellent therapeutic method for NP is desired.

Multiple sclerosis (hereinafter referred to as MS) is a disease that has a focus generated in a central nerve system such as a brain or a spinal cord, and causes various neurological symptoms (such as visual disturbance, dyskinesia, hypesthesia, dysesthesia, pain, dysequilibrium, shivering, dysuria, sexual dysfunction, fatigue, and emotional disorder). MS is divided, depending on the progressive mode of a patient's condition, into a "relapsing-remitting type" wherein relapse and remission are repeated, and a "chronic progressive type" that the symptom is gradually worsened. The chronic progressive type is further divided into a "secondary progressive type" that the relapsing-remitting MS subsequently shows chronic progression, and a "primary progressive type" that obvious relapse does not occur but the symptom is gradually worsened from the initial stage of the onset.

The cause of MS has not been elucidated yet. There is a report about the cause of MS that T cells or macrophages infiltrate into nerve tissues and attack the patient's own myelin covering axon of nerve cells of the brain or the spinal cord, and as a result, inflammation is caused in the myelin and hence demyelination is caused, which leads to MS (Non Patent Document 2)

A therapeutic method for MS is divided into three categories, that is, inhibition of inflammation in an acute period, inhibition of relapse or progression, and relief of the symptoms.

In a treatment in an acute period, glucocorticoid (a steroid anti-inflammatory drug) is used to inhibit the inflammation of a site where the myelin is damaged. MS is a disease difficult to completely recover because relapse and remission repeatedly occur. Various immunological treatments based on the pathogenetic mechanism of MS have been studied (Non Patent Document 2), and it is presumed that interferon β and immunosuppressive agents are effective. However, a sufficiently effective and safe therapeutic method has not been established. In particular, an excellent therapeutic method for MS at the time of relapse is desired.

MIF is a cytokine secreted from activated lymphocytes and having various biological activities. It is known to exhibit activities for, for example, an immune system, an endocrine system, and proliferation and differentiation of cells. Particularly, MIF plays a significant role in systemic inflammation and immune response, and is a factor pertaining also to a delayed hypersensitivity reaction for inhibiting random migration of macrophages. Besides, MIF has dopachrome tautomerase activity (Non Patent Document 3).

On the other hand, MIF is known to have homology to glutathione S-transferase, to show detoxification, to be secreted from adenohypophysis at the time of endotoxic shock, to be induced by a low level of glucocorticoid, and to oppose its immunosuppressive effect (Non Patent Document 4). In other words, MIF inhibits the activity of glucocorticoid, antagonizes the anti-inflammatory effect of endogenous or therapeutically administered glucocorticoid, and works also as a cause or an aggravating factor of an inflammatory disease and an inflammatory state.

Besides, MIF is indispensable for activation of T cells, is expressed in various cells, and is strongly expressed particularly in the nerve system.

In the relation between MIF and diseases, for example, an MIF inhibitor relieves an allodynia symptom of an animal model for NP. On the other hand, a mouse model showing a stimulus sensitivity reaction aggravated by stress can be produced by injecting recombinant MIF to a normal mouse (Non Patent Document 5). Besides, in an animal model for NP, specifically, in a model for the allodynia induced by sciatic nerve ligation, MIF is highly expressed in the ipsilateral dorsal horn of spinal cord, and signaling molecules on the downstream side from MIF are activated (Non Patent Document 6). Furthermore, in an MIF knockout mouse, the allodynia induced by sciatic nerve ligation is eliminated (Non Patent Documents 5 and 6). Accordingly, MIF is presumed to be indispensable for expression of the symptoms of NP.

On the other hand, in an MS patient, the MIF concentration in a cerebrospinal fluid is significantly increased at the time of relapse, when compared to the time of remission (Non Patent Document 7). Besides, experimental autoimmune encephalomyelitis (hereinafter referred to as EAE) of a mouse, that is, a model animal for MS, can be prevented for the relapse by knocking out MIF genes (Non Patent Document 8). It is obvious from these facts that MIF plays an extremely significant role in the formation of NP and MS.

EAE, that is, the animal model for MS, includes a model for reproducing primary onset of an acute period (monophasic) and a model for reproducing chronic relapsing/remitting condition, and in general, rats are used for the former and mice are used for the latter to construct the model.

It is reported, for example, that cyclophosphamide of an immunosuppressive agent inhibits the onset of acute EAE in rats but is ineffective for relapsing type or chronic progressive type of EAE in mice (Non Patent Document 9).

It is also reported that a rat or mouse anti-α4 integrin antibody equivalent to an MS therapeutic agent, natalizumab, delayed the onset and reduced the severity of the disease with respect to the acute EAE in rats, and inhibited the EAE onset in mice by administration for preventing EAE, but the symptoms were aggravated by therapeutic administration (Non Patent Documents 10 and 11).

A benzopyran derivative exhibits an antiarthritic effect (Patent Document 1), an inhibitory effect for production of inflammatory cytokines, such as interleukin-1β and interleukin-6, and an immunomodulatory effect (Non Patent Documents 12, 13 and 14), and is known to be useful for a treatment of rheumatoid arthritis and other arthritis, and autoimmune diseases (Patent Document 2). Besides, it is known to be effective for the acute EAE in rats (Non Patent Document 15).

It is, however, not known at all that the benzopyran derivative binds to MIF to inhibit its biological activities, as mentioned above.

Besides, the effectiveness of the benzopyran derivative for NP as mentioned above is not known at all, and the effectiveness thereof for the relapsing-remitting or secondary progressive MS at the time of relapse is also not known at all.

PRIOR ART DOCUMENTS

Patent Document

Patent Document 1: JP 02-049778 A
Patent Document 2: Pamphlet of International Publication No. WO 94/23714

Non Patent Document

Non Patent Document 1: Lancet, 1999, vol. 353, pp. 1959-1964
Non Patent Document 2: N. Engl. J. Med., 2000, vol. 343, pp. 938-952
Non Patent Document 3: Nat. Rev. Drug Discov., 2006, vol. 5, pp. 399-410
Non Patent Document 4: Molecular Medicine, 1996, vol. 2, pp. 143-149
Non Patent Document 5: Exp. Neurol., 2012, vol. 236, pp. 351-362
Non Patent Document 6: Anesthesiology, 2011, vol. 114, pp. 643-659
Non Patent Document 7: J. Neurol. Sci., 2000, vol. 179, pp. 127-131
Non Patent Document 8: J. Immunol., 2005, vol. 175, pp. 5611-5614
Non Patent Document 9: Clin. Exp. Immunol., 2009, vol. 159, pp. 159-168
Non Patent Document 10: J. Pharmacol. Exp. Ther., 2003, vol. 305, pp. 1150-62
Non Patent Document 11: J. Clin. Invest., 2001, vol. 107, pp. 995-1006
Non Patent Document 12: Chem. Pharm. Bull., 2000, vol. 48, pp. 131-139
Non Patent Document 13: J. Pharamcobiodyn., 1992, vol. 15, pp. 649-655
Non Patent Document 14: Int. J. Immunotherapy, 1993, vol. 9, pp. 69-78
Non Patent Document 15: J. Neuroimmunol., 1998, vol. 89, pp. 35-42

SUMMARY OF INVENTION

Technical Problem

A medical product useful for a therapeutic or preventive treatment of diseases such as NP and MS is desired, and a pharmaceutical composition for inhibiting MIF, that is, a factor significant as the cause of these diseases, is desired.

In particular, a pharmaceutical composition useful for a therapeutic or preventive treatment of NP, relapsing MS and the like is desired.

Solution to Problem

Under these circumstances, the present inventors found that a benzopyran derivative represented by the following general formula [1] or a salt thereof binds to MIF, exhibits an MIF inhibitory effect, and hence is useful for a therapeutic or preventive treatment of a disease for which the inhibition of MIF is effective, resulting in accomplishing the present invention:

[Formula 1]

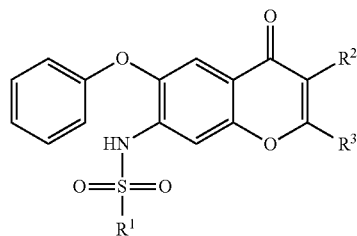

[1]

wherein $R^1$ represents an optionally substituted $C_{1-6}$ alkyl group; one of $R^2$ and $R^3$ represents a hydrogen atom; and the other of $R^2$ and $R^3$ represents a hydrogen atom, an optionally substituted amino group, an optionally substituted acylamino group, an optionally substituted carbamoyl group or an optionally substituted aryl group.

Advantageous Effects of Invention

A benzopyran derivative represented by general formula [1] or a salt thereof exhibits an MIF inhibitory effect and is useful for a therapeutic or preventive treatment of diseases for which the inhibition of MIF is effective, such as NP and the relapsing-remitting and secondary progressive MS at the time of relapse.

DESCRIPTION OF EMBODIMENTS

The present invention will be described below in detail.

The terms as used herein have the following meanings unless otherwise noted.

A halogen atom means a fluorine atom, a chlorine atom, a bromine atom or an iodine atom.

A $C_{1-6}$ alkyl group means a linear or branched $C_{1-6}$ alkyl group such as a methyl group, an ethyl group, a propyl group, an isopropyl group, a butyl group, a sec-butyl group, an isobutyl group, a tert-butyl group, a pentyl group, an isopentyl group and a hexyl group.

A $C_{1-6}$ alkoxy group means a linear or branched $C_{1-6}$ alkyloxy group such as a methoxy group, an ethoxy group, a propoxy group, an isopropoxy group, a butoxy group, an isobutoxy group, a sec-butoxy group, a tert-butoxy group, a pentyloxy group and a hexyloxy group.

A $C_{2-12}$ alkanoyl group means a linear or branched $C_{2-12}$ alkanoyl group such as an acetyl group, a propionyl group, a valeryl group, an isovaleryl group and a pivaloyl group.

An aroyl group means a benzoyl group or a naphthoyl group.

A heterocyclic carbonyl group means a nicotinoyl group, a tenoyl group, a pyrrolizinocarbonyl group or a furoyl group.

An (α-substituted) aminoacetyl group means an (α-substituted) aminoacetyl group which is derived from an amino acid (such as glycine, alanine, valine, leucine, isoleucine, serine, threonine, cysteine, methionine, aspartic acid, glutamic acid, asparagine, glutamine, arginine, lysine, histidine, hydroxylysine, phenylalanine, tyrosine, tryptophan, proline and hydroxyproline) and which may have a protected N-terminal.

An acyl group means a formyl group, a succinyl group, a glutaryl group, a maleoyl group, a phthaloyl group, a $C_{2-12}$ alkanoyl group, an aroyl group, a heterocyclic carbonyl group or an (α-substituted) aminoacetyl group.

An acylamino group means an amino group substituted with an acyl group.

An aryl group means a phenyl group, a naphthyl group, an indanyl group, an indenyl group, a tetrahydronaphthyl group or the like.

The $C_{1-6}$ alkyl group of $R^1$ may be substituted with one or more halogen atoms.

The amino group or the carbamoyl group of $R^2$ and $R^3$ may be substituted with one or more $C_{1-6}$ alkyl groups.

The acylamino group of $R^2$ and $R^3$ may be substituted with one or more halogen atoms.

The aryl group of $R^2$ and $R^3$ may be substituted with one or more groups selected from a halogen atom, an amino group, a hydroxyl group, a $C_{1-6}$ alkyl group which may be substituted with one or more halogen atoms, and a $C_{1-6}$ alkoxy group which may be substituted with one or more halogen atoms.

Preferable examples of the benzopyran derivative represented by general formula [1] of the present invention include compounds described below.

A compound in which $R^1$ is an optionally substituted $C_{1-6}$ alkyl group; one of $R^2$ and $R^3$ is a hydrogen atom; and the other of $R^2$ and $R^3$ is an optionally substituted acylamino group is preferred.

Specifically, N-[7-[(methylsulfonyl)amino]-4-oxo-6-phenoxy-4H-1-benzopyran-3-yl]formamide, N-(3-amino-4-oxo-6-phenoxy-4H-1-benzopyran-7-yl)methanesulfonamide, N-[7-[(methylsulfonyl)amino]-4-oxo-6-phenoxy-4H-1-benzopyran-3-yl]acetamide, N-(4-oxo-6-phenoxy-4H-1-benzopyran-7-yl)methanesulfonamide, 7-[(methylsulfonyl)amino]-4-oxo-6-phenoxy-4H-1-benzopyran-2-carboxamide, N-[7-[(methylsulfonyl)amino]-4-oxo-6-phenoxy-4H-1-benzopyran-2-yl]acetamide, 7-[(methylsulfonyl)amino]-4-oxo-6-phenoxy-4H-1-benzopyran-3-carboxamide, N-[7-[(ethylsulfonyl)amino]-4-oxo-6-phenoxy-4H-1-benzopyran-3-yl]formamide, and N-(4-oxo-6-phenoxy-2-phenyl-4H-1-benzopyran-7-yl) methanesulfonamide are preferred, and N-[7-[(methylsulfonyl)amino]-4-oxo-6-phenoxy-4H-1-benzopyran-3-yl]formamide is more preferred.

The benzopyran derivative of general formula [1] used in the present invention is produced by combining the publicly acknowledged methods, and can be produced by, for example, a method described in Patent Document 1.

Examples of the salt of the benzopyran derivative of general formula [1] include a salt with an alkali metal such as sodium or potassium; a salt with an alkali earth metal such as calcium and magnesium; an ammonium salt; and a salt with a nitrogen-containing organic base such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-efenamine and N,N'-dibenzylethylenediamine.

Among the aforementioned salts, pharmacologically acceptable salts are preferred.

MIF has high homology to a bacterial tautomerase, and catalyzes a dopachrome tautomerase reaction (Molecular Medicine, 1996, vol. 2, pp. 143-149). Therefore, the biological activity of MIF can be evaluated by using a tautomerase reaction with a dopachrome as a substrate.

The benzopyran derivative of general formula [1] or the salt thereof of the present invention has an effect to inhibit the MIF tautomerase activity (namely, an MIF inhibitory effect), and a drug containing the benzopyran derivative of general formula [1] or the salt thereof is useful for a therapeutic or preventive treatment of diseases for which the MIF inhibition is effective.

Examples of the disease for which the MIF inhibition is effective include NP and the relapsing-remitting and secondary progressive MS at the time of relapse, and preferably include NP.

Examples of NP include fibromyalgia, postherpetic pain, diabetic neuropathy, post-spinal cord injury pain, postapoplectic pain, chronic pain, complex regional pain syndrome, backache for which NSAIDs are insufficiently effective, sciatica, pelvic pain, trigeminal neuralgia, osteoarthritis pain for which NSAIDs are insufficiently effective, deafferentation pain syndrome, pain due to myositis, pain due to fasciitis, and pain due to seronegative arthritis. Examples of the deafferentation pain syndrome include thalamic pain, pain due to MS, pain after avulsion injury, phantom limb pain, and postoperative pain syndrome. Examples of the pain due to seronegative arthritis include pain due to axial joint disorder, pain due to ankylosing spondylitis, pain due to sacroiliac joint disorder, and pain due to seronegative spondylitis.

Preferable examples include fibromyalgia, postherpetic pain, diabetic neuropathy, backache for which NSAIDs are insufficiently effective, osteoarthritis pain for which NSAIDs are insufficiently effective, pain due to myositis, pain due to fasciitis, and pain due to seronegative arthritis, and more preferable examples include postherpetic pain, diabetic neuropathy, backache for which NSAIDs are insufficiently effective, osteoarthritis pain for which NSAIDs are insufficiently effective, pain due to myositis, pain due to fasciitis, and pain due to seronegative arthritis.

The relapsing-remitting MS has a characteristic that it is ameliorated over several weeks or several months after a neurological symptom having acutely appeared reaches the fastigium, and then it relapses to reproduce or aggravate the neurological symptom. A remission period follows the relapse. A relapse occurred every several months or years and a slow or gradual remission are repeated.

The secondary progressive MS has a characteristic that a remission state of a patient having initially developed the relapsing-remitting MS is gradually aggravated while the relapse and the remission are repeated.

Examples of the symptoms of the relapsing-remitting MS and secondary progressive MS at the time of relapse include reduced vision, motor paralysis, sensory disturbance, multiple vision, dysuria and dysarthria.

The compound of the present invention can be formed into pharmaceutical formulations such as an oral preparation (including a tablet, a capsule, a powder, a granule, a fine granule, a pill, a suspension, an emulsion, a liquid and a syrup), an injection and an eye drop by mixing with various pharmaceutical additives such as an excipient, a binder, a disintegrant, a disintegration inhibitor, an anti-caking agent, a lubricant, a carrier, a solvent, an expander, a tonicity adjusting agent, a solubilizing agent, an emulsifier, a suspending agent, a thickener, a coating agent, an absorption enhancer, a gelling enhancer, a coagulation accelerator, a light stabilizer, a preservative, a desiccating agent, an emulsion stabilizer, a suspension stabilizer, a dispersion stabilizer, a coloring inhibitor, an oxygen absorber, an antioxidant, a taste masking agent, an odor masking agent, a coloring agent, a foaming agent, an antifoaming agent, a soothing agent, an antistatic agent, a diluent, a pH buffer, and a pH adjustor.

The above-described various formulations are formulated by usual methods.

An oral solid formulation such as a tablet, a powder and a granule may be formulated by a usual method using a pharmaceutical additive of, for example, an excipient such as lactose, saccharose, sodium chloride, glucose, starch, calcium carbonate, kaolin, crystalline cellulose, anhydrous dibasic calcium phosphate, partly pregelatinized starch, corn starch and alginic acid; a binder such as a simple syrup, a glucose solution, a starch solution, a gelatin solution, polyvinyl alcohol, polyvinyl ether, polyvinyl pyrrolidone, carboxymethyl cellulose, shellac, methyl cellulose, ethyl cellulose, sodium alginate, acacia, hydroxypropyl methyl cellulose and hydroxypropyl cellulose; a disintegrant such as dry starch, alginic acid, powdered agar, starch, cross-linked polyvinyl pyrrolidone, cross-linked carboxymethyl cellulose sodium, carboxymethyl cellulose potassium and sodium starch glycolate; a disintegration inhibitor such as stearyl alcohol, stearic acid, cacao butter and hydrogenated oil; an anti-caking agent such as aluminum silicate, calcium hydrogen phosphate, magnesium oxide, talc and silicic anhydride; a lubricant such as carnauba wax, light anhydrous silicic acid, aluminum silicate, magnesium silicate, a hydrogenated oil, a hydrogenated vegetable oil derivative, sesame oil, white beeswax, titanium oxide, dried aluminum hydroxide gel, stearic acid, calcium stearate, magnesium stearate, talc, calcium hydrogen phosphate, sodium lauryl sulfate and polyethylene glycol; an absorption enhancer such as a quaternary ammonium salt, sodium lauryl sulfate, urea and an enzyme; and a carrier such as starch, lactose, kaolin, bentonite, silicic anhydride, hydrated silicon dioxide, magnesium aluminometasilicate and colloidal silicic acid.

The tablet may be formed, if necessary, into a general coated tablet, such as a sugar coated tablet, a gelatin coated tablet, a gastric soluble coated tablet, an enteric coated tablet and a water-soluble film coated tablet.

The capsule is prepared by filling a hard gelatin capsule, a soft capsule and the like with any of the aforementioned various pharmaceutical additives.

Alternatively, a pharmaceutical additive such as a solvent, an expander, a tonicity adjusting agent, a solubilizing agent, an emulsifier, a suspending agent and a thickener may be used for preparation by a usual method to obtain an aqueous or oil suspension, a solution, a syrup and an elixir.

The injection may be prepared by a usual method using a pharmaceutical additive of, for example, a diluent such as water, ethyl alcohol, macrogol, propylene glycol, citric acid, acetic acid, phosphoric acid, lactic acid, sodium lactate, sulfuric acid and sodium hydroxide; a pH buffer and a pH adjuster such as sodium citrate, sodium acetate and sodium phosphate; an emulsion stabilizer, a suspension stabilizer and a dispersion stabilizer such as sodium pyrosulfite, ethylenediaminetetraacetic acid, thioglycolic acid and thiolactic acid; a tonicity adjusting agent such as common salt, glucose, mannitol and glycerin; a solubilizing agent such as carboxymethyl cellulose sodium, propylene glycol, sodium benzoate, benzyl benzoate, urethane, ethanolamine and glycerin; a soothing agent such as calcium gluconate, chlorobutanol, glucose and benzyl alcohol; and a local anesthetic.

The eye drop may be prepared by a usual method by appropriately mixing with a preservative such as chlorobutanol, sodium dehydroacetate, benzalkonium chloride, cetylpyridinium chloride, phenethyl alcohol, methyl paraoxybenzoate and benzethonium chloride; a pH buffer and a pH adjustor such as borax, boric acid and potassium dihydrogenphosphate; a thickener such as methyl cellulose, hydroxyethyl cellulose, carboxymethyl cellulose, hydroxypropyl methyl cellulose, polyvinyl alcohol, carboxymethyl cellulose sodium and chondroitin sulfate; a solubilizing agent such as polysorbate 80 and polyoxyethylene hardened castor oil 60; an emulsion stabilizer, a suspension stabilizer and a dispersion stabilizer such as sodium edetate and sodium hydrogen sulfite; and a tonicity adjusting agent such as sodium chloride, potassium chloride and glycerin.

An administration method of the formulation is not especially limited, and is appropriately determined in accordance with the form of the formulation, the age, sex and other conditions of a patient, and the degree of the symptom of the patient.

A dose of an active ingredient of the present formulation is appropriately selected in accordance with the usage, the age and sex of a patient, the form of a disease and the other conditions, and generally, it may be administered at a dose of 0.1 to 500 mg, preferably 10 to 200 mg per day once or dividedly several times a day for an adult.

EXAMPLES

Next, the present invention will be described with reference to test examples, and it is noted that the present invention is not limited to these examples.

Abbreviations used in the respective test examples have the following meanings.

MES: 2-(N-morpholino)ethanesulfonic acid
DMF: N,N-dimethylformamide

EDC: 1-ethyl-3-(3-dimethylaminopropyl)carbodiimide hydrochloride
EDTA: ethylenediaminetetraacetic acid
NHS: N-hydroxysuccinimide
PLP: Proteolipid protein
TBST: Tween 20-containing Tris-buffered saline
The following compounds were used as test substances.

TABLE 1

| Compound | $R^1$ | $R^2$ | $R^3$ |
|---|---|---|---|
| Compound A | $CH_3$ | NHCHO | H |
| Compound B | $CH_3$ | $NH_2$ | H |
| Compound C | $CH_3$ | $NHCOCH_3$ | H |
| Compound D | $CH_3$ | H | H |
| Compound E | $CH_3$ | H | $CONH_2$ |
| Compound F | $CH_3$ | H | $NHCOCH_3$ |
| Compound G | $CH_3$ | $CONH_2$ | H |
| Compound H | $CH_3CH_2$ | NHCHO | H |
| Compound I | $CH_3$ | H | phenyl |

Test Example 1 (Confirmation of the Binding of Compound A and MIF)

As a test substance, Compound A (N-[7-[(methylsulfonyl)amino]-4-oxo-6-phenoxy-4H-1-benzopyran-3-yl]formamide) was used.

(1) Preparation of Cell Lysate

THP-1 cells were cultured for about 6 hours in PRMI 1640 medium containing 1% fetal bovine serum and 50 μmol/L 2-mercaptoethanol. Then, lipopolysaccharide (*E. coli* 0127:B8, Sigma Aldrich) was added to the culture plate at a final concentration of 1 μg/mL, and the cells were cultured for about 30 minutes. The cells were harvested and washed with phosphate buffered saline, and mixed with about 2-fold volume of cell lysis buffer (20 mmol/L Tris, 150 mmol/L sodium chloride, 1 mmol/L magnesium chloride, 0.1% NP-40, 1 mmol/L dithiothreitol, 0.1% Triton X-100, pH 7.4). The resultant mixture was placed on ice with occasional stirring for about 30 minutes, and was centrifuged (20000×g, 4° C., 8 minutes). The separated and gained supernatant was used as cell lysate. Protein concentration of the cell lysate was measured with BCA protein assay reagent (Thermo Fisher Scientific K.K.) in accordance with its manual.

(2) Synthesis of 4-amino-N-[7-[(methylsulfonyl)amino]-4-oxo-6-phenoxy-4H-1-benzopyran-3-yl]butanamide hydrochloride To a solution of 500 mg of N-(3-amino-4-oxo-6-phenoxy-4H-1-benzopyran-7-yl)methanesulfonamide in 5.0 mL of DMF, 293 mg of 4-(tert-butoxycarbonylamino)butyric acid and 304 mg of EDC were added, followed by stirring at room temperature for 1 hour and 30 minutes. To the thus obtained reaction mixture, 111 mg of EDC was added, followed by stirring at room temperature for 3 hours and 30 minutes. Ethyl acetate and 10% citric acid aqueous solution were added to the resulting reaction mixture, the resultant was stirred at room temperature for 30 minutes, and a solid was filtered. To the thus obtained solid, DMF, ethyl acetate and 10% citric acid aqueous solution were added, followed by stirring at room temperature for 1 hour. Then, the solid was filtered to obtain 397 mg of tert-butyl [4-[[7-[(methylsulfonyl)amino]-4-oxo-6-phonoxy-4H-1-benzopyran-3-yl]amino]-4-oxobutyl]carbamate in the form of a pale yellow solid. 300 mg of the thus obtained tert-butyl [4-[[7-[(methylsulfonyl)amino]-4-oxo-6-phenoxy-4H-1-benzopyran-3-yl]amino]-4-oxobutyl]carbamate was suspended in 3.0 mL of methylene chloride, 0.60 mL of trifluoroacetic acid was added thereto under ice cooling, the resultant was stirred at room temperature for 40 minutes, and then the solvent was distilled off under reduced pressure. To the thus obtained residue, 3 mL of ethyl acetate and 0.25 mL of 4 mol/L hydrogen chloride/ethyl acetate solution were added, and the solvent was distilled off under reduced pressure. To the thus obtained residue, 5.0 mL of ethyl acetate and 0.50 mL of 4 mol/L hydrogen chloride/ethyl acetate solution were added, followed by stirring at room temperature for 2 hours. Then, a solid was filtered to obtain 232 mg of 4-amino-N-[7-[(methylsulfonyl)amino]-4-oxo-6-phenoxy-4H-1-benzopyran-3-yl]butanamide hydrochloride as a pale yellow solid.

(3) Preparation of Beads

Immobilization of 4-amino-N-[7-[(methylsulfonyl)amino]-4-oxo-6-phenoxy-4H-1-benzopyran-3-yl]butanamide hydrochloride on Dynabeads M-270 Carboxylic Acid (Life Technologies Corporation) was performed by a general method.

Briefly, after NHS esterifying COOH terminals of about 30 mg of the beads (Dynabeads M-270 Carboxylic Acid, Life Technologies Corporation), 0.010 mL of DMF, 0.90 mL of 0.01 mol/L 4-amino-N-[7-[(methylsulfonyl)amino]-4-oxo-6-phenoxy-4H-1-benzopyran-3-yl]butanamide hydrochloride/DMF solution, and 0.090 mL of 1 mol/L N,N-diisopropylethylamine/DMF solution were added thereto, and the resultant was shook at room temperature for 70 minutes. The beads were washed with 0.5 mL of DMF twice, and then, 0.94 mL of DMF and 0.060 mL of 2-aminoethanol were added thereto, followed by shaking at room temperature for 2 hours. The beads were washed with 0.5 mL of DMF twice, and then washed with 1 mL of 0.05 mol/L phosphate buffer (pH 6) four times, and thus, beads to which Compound A was bound via a linker were obtained (hereinafter referred to as the compound beads). Besides, beads obtained by a similar reaction without adding 4-amino-N-[7-[(methylsulfonyl)amino]-4-oxo-6-phenoxy-4H-1-benzopyran-3-yl]butanamide hydrochloride were used as control beads. Each type of these beads was suspended in 1 mL of 0.05 mol/L phosphate buffer (pH 6) to be stored in a refrigerator until use. Just before use, a part of the beads was separated and washed with cell lysis buffer three times.

(4) Reaction Between Cell Extract and Beads 0.1 mL of cell lysate (2 mg/mL of protein) and about 0.9 mg of the compound beads or control beads were thoroughly mixed overnight at 4° C. Supernatants were separated from the beads by using a magnet, and were collected as Flow-through fraction. Besides, the beads were rinsed with cell lysis buffer, and then were reacted with 40 μL of cell lysis buffer containing 0.5 mmol/L of Compound A at 4° C. for about 8 hours with vigorous stirring. Supernatants were separated from the beads by using a magnet, and were collected as Compound A-eluate. Moreover, the beads were lightly rinsed with cell lysis buffer, were mixed with 154 of SDS-PAGE sample buffer (2ME+) (Wako Pure Chemical Industries, Ltd.), which had been diluted to 4 times, and were heated at about 95° C. for 5 minutes. Thereafter, supernatants separated from the beads by using a magnet were collected as Heat-eluted fraction.

(5) Detection of MIF by Western Blotting

Western blotting was carried out by a general method.

Both of a part of the Flow-through fraction and a part of the Compound A-eluate obtained as described above in (4) were respectively mixed with the SDS-PAGE sample buffer (2ME+), and were heated. These heat-treated samples and the Heat-eluted fraction were electrophoresed on SDS-PAGE gel (SuperSep Ace 15%, Wako Pure Chemical Industries, Ltd.) at 30 to 50 mA for about 80 minutes, and then were electrophoretically transferred to a PVDF membrane (Hybond-P, GE Healthcare Japan Corporation) at 100 mA for about 60 minutes. The protein-transferred membrane was immersed and gently shaken in TBST solution (10 mmol/L Tris, 100 mmol/L sodium chloride, 0.1% Tween-20, pH 7.5) containing 5% skim milk at room temperature for about 1 hour. Thereafter, the membrane was immersed in TBST solution containing 1/50000 volume of anti-MIF antibody (Abcam Plc.) and 5% skim milk, and was reacted overnight at 4° C. with gentle mixing. After lightly rinsing the membrane with TBST solution three times, the resultant membrane was immersed in TBST solution containing 1/5000 volume of HRP-modified anti-goat IgG antibody (Santa Cruz Biotechnology Inc.) and 5% skim milk, and was reacted at room temperature for 1 hour with gentle mixing. After lightly rinsing the membrane with TBST solution three times, MIF was detected by using ECL Prime reagent (GE Healthcare Japan Corporation) in accordance with its manual.

FIG. 1 shows a photograph of the membrane on which binding reactants of MIF and the antibody are detected by chemiluminescence.

Fractions electrophoresed in respective lanes of the gel were as follows:
Lane 1: Flow-through fraction of the compound beads
Lane 2: Compound A-eluate of the compound beads
Lane 3: Heat-eluted fraction of the compound beads
Lane 4: recombinant MIF (Abcam Plc.)
Lane 5: Flow-through fraction of the control beads
Lane 6: Compound A-eluate of the control beads
Lane 7: Heat-eluted fraction of the control beads The Compound A-eluate of the compound beads contains proteins that have binding capacity to the compound beads and is relieved from the compound beads in the presence of an excessive amount of Compound A. A band detected in the Compound A-eluate (i.e., Lane 2) was proved to be MIF because it was bound to the anti-MIF antibody and was in a position corresponding to the same molecular weight as recombinant MIF.

In other words, it was revealed that MIF has binding capacity to the compound beads.

On the other hand, both of the Compound A-eluate of the control beads and the Heat-eluted fraction of the control beads contain proteins having binding capacity to the control beads. Since MIF was not detected in these fractions (namely, Lanes 6 and 7), it was shown that MIF has no binding capacity to the control beads.

Accordingly, it was proved that MIF specifically binds to Compound A.

Test Example 2 (Confirmation of Inhibition of MIF Activity)

Compounds A to I were used as test substances.

The inhibitory effect of test substances against tautomerase activity of MIF was evaluated by referring to a method of Healy et al. (Cancer Epidemiology Biomarkers and Prevention, 2011, vol. 20, pp. 1516-1523).

In this method, tautomeric reaction from L-3,4-dihydroxyphenylalanine methyl ester (L-dopachrome methyl ester, colored) to 5,6-hydroxyindole-2-carboxylic acid methyl ester (no color) is measured as a change in absorbance at 475 nm.

As an enzyme source, recombinant MIF manufactured by Abcam Plc. or MIF produced and purified by referring to a method of Lubetsky et al. (The Journal of Biological Chemistry, 2002, vol. 277, pp. 24976-24982) was used. A purification method for MIF is described below.

The pET15b vector (Merck) into which the full length gene sequence of MIF had been inserted was transfected $E.$ $coli$ BL21 Star (DE3) strain (Life Technologies Corporation). The $E.$ $coli$ was cultured until the culture medium exhibited absorbance (at 600 nm) of 0.5 to 0.8, isopropyl-β-thiogalactopyranoside (Wako Pure Chemical Industries, Ltd.) was added thereto to a final concentration of 0.1 mmol/L, and the protein expression was induced for 4 hours. The $E.$ $coli$ were resuspended in buffer (pH 7.5) containing 20 mmol/L Tris (Wako Pure Chemical Industries, Ltd.), 20 mmol/L sodium chloride (Wako Pure Chemical Industries, Ltd.) and 1 mmol/L dithiothreitol (Wako Pure Chemical Industries, Ltd.), and the resultant was subjected to ultrasonic lysis and centrifugation at 15000 rpm for 10 minutes. The thus obtained supernatant was filtered using a 0.20 μm filter, and was allowed to pass through HiTrap Q HP and HiTrap SP HP columns (GE Healthcare Japan Corporation), so as to separate flow-through fractions each of 5 mL. Each of 10 μL of the separated fractions was subjected to the electrophoresis using 5 to 20% polyacrylamide gel (Wako Pure Chemical Industries, Ltd.), and all proteins were stained with Coomassie brilliant blue reagent (Bio-Rad Laboratories, Inc.). On the basis of results thus obtained, a fraction containing a large amount of MIF and containing least amount of other proteins was selected as purified MIF. The concentration of MIF protein was measured by using BCA protein assay reagent (Thermo Fisher Scientific K. K.).

Inhibitory effect of each test substance against MIF tautomerase activity was measured as follows.

A final concentration of 10 to 50 nmol/L of MIF and a final concentration of 30 μmol/L of each test substance or 0.5% dimethyl sulfoxide (Wako Pure Chemical Industries, Ltd.) as a control were added to buffer (pH 6.2) containing 50 mmol/L Bis-Tris (Dojindo Laboratories) and 1 mmol/L EDTA (Dojindo Laboratories), and reaction was performed at room temperature for 15 minutes to give a reaction solution 1.

On the other hand, 1/20 volume of 12 mmol/L L-3,4-dihydroxyphenylalanine methyl ester (Sigma Aldrich) and 1/20 volume of 24 mmol/L sodium periodate (Wako Pure Chemical Industries, Ltd.) were added to buffer having the same composition as that used for obtaining the reaction solution 1, to give a reaction solution 2.

Next, the reaction solution 1 and the reaction solution 2 were mixed, and the temporal change of absorbance at 475 nm of the obtained mixture was immediately measured.

The difference of the absorbencies between the at about 1 minute after the measurement start and at about 5 minutes after was obtained. Assuming that the absorbance change of the control is 100%, an inhibiting rate of the tautomerase reaction in presence of each test substance was calculated.

The results are shown in Table 2. In Table 2, the tautomerase reaction inhibiting rate is shown as follows. "−"; less than 50%, "+"; 50% or more and less than 75%, "++"; 75% or more.

TABLE 2

| Test Substance | Inhibition Rate of Tautomerase Reaction |
|---|---|
| Compound A | + |
| Compound B | + |
| Compound C | + |
| Compound D | + |
| Compound E | ++ |
| Compound F | ++ |
| Compound G | + |
| Compound H | ++ |
| Compound I | ++ |

All of the test substances inhibited the tautomerase activity of MIF.

The above-described results reveal that the compound of general formula [1] or the salt thereof show the MIF inhibitory effect and is useful as an MIF inhibitor.

Test Example 3 (Effect of Compound A on Chronic Constriction Nerve Injury Model Rat)

This test was performed by referring to a method of Bennett et al. (Pain, 1988, vol. 33, pp. 87-107).

Compound A was used as a test substance, and celecoxib, one of NSAIDs, was used as a reference substance. The compound A was administered at a dose of 30 mg/kg (Compound A group). The celecoxib was administered at a dose of 30 mg/kg (celecoxib group). To a control group, a 0.5% methyl cellulose aqueous solution used as a vehicle was administered.

Under anesthetic with Somnopentyl (manufactured by Kyoritsu Seiyaku Corporation, about 52 mg/kg, intraperitoneal administration), nerve constriction operation was performed on the left sciatic nerves of Sprague-Dawley male rats (7 weeks old). Briefly, a left femoral region of each rat was dissected, the sciatic nerve was detached from tissues around, and the nerve was loosely constricted with a 4-0 silk suture (manufactured by Eticon Inc., surgical silk) for having narrow parts in four positions at intervals of about 1 mm. The muscular layer and the skin were respectively sutured, and the operation region was disinfected. The vehicle, the test substance or the reference substance was orally administered once a day continuously for 14 days from the 16th day after the operation.

From the start of the administration, pain sense (mechanical allodynia) of the footpad of left hind paw was evaluated by von Frey test. Briefly, von Frey filaments respectively having various flexibilities (Semmes-Weinstein Von Frey Anesthesiometer (manufactured by Danmic Global, LCC)) were vertically pressed against the footpad of the left hind paw successively in order from one having a lightest elasticity, and the elastic force of the filament against which the rat showed a withdrawal response was determined as a pain threshold value.

The evaluation of the pain sense was expressed as an average of pain threshold values. The results are shown in Table 3.

TABLE 3

| Test group | Number of animals | Average of pain thresholds (g) | |
|---|---|---|---|
| | | 15th day after operation | 30th day after operation |
| Control group | 8 | 2.7 | 4.2 |
| Compound A group | 8 | 2.4 | 13.5 |
| Celecoxib group | 7 | 2.5 | 3.1 |

The pain threshold value of the Compound A group was increased to 13.5 g 14 days after the start of the administration (on the 30th day after the operation), and thus, Compound A inhibited the symptom of the mechanical allodynia as compared with that in the control group.

On the other hand, the administration of celecoxib (30 mg/kg), NSAID, did not suppress the mechanical allodynia symptom.

The above-described results reveal that Compound A suppresses the symptom of the mechanical allodynia by a mechanism different from that of NSAIDs.

Test Example 4 (Effect on Chronic Relapsing EAE Model of Mouse)

Compound A was selected as a test substance, and salazosulfapyridine (hereinafter referred to as SASP) was selected as a comparative control agent. Compound A was administered at a dose of 30 mg/kg (Compound A group). SASP was administered at a dose of 300 mg/kg (SASP group). In control group and normal group (no induction treatment group), 0.5% methyl cellulose aqueous solution used as vehicle of the administration liquid was administered.

The chronic relapsing EAE was induced in SJL/J female mice by immunization with partial PLP peptide. Briefly, an emulsion was prepared by mixing equivalent volumes of phosphate buffer saline containing 1 mg/mL of the peptide corresponding to residues 139-151 of the PLP and Freund's incomplete adjuvant containing 4 mg/mL of killed M. Tuberculosis H37Ra. The emulsion was intradermically injected (50 µg of PLP per mouse) into four positions on the back for immunization, and additionally, on the day of the immunization and two days after, pertussis toxin was intraperitoneally injected in each amount of 150 ng per mouse, twice in total. The vehicle, the test substance or the reference article was orally administered continuously for 44 days once daily from the day of the immunization.

In the present experiment, paralysis was developed to reach a peak on the 14th to 16th day after the immunization, and the symptom remitted once, but relapsed to reach a peak on the 38th day.

The symptom was evaluated in accordance with a report of Weaver et al. (FASEB Journal, 2005, vol. 19, p. 1668). Briefly, paralysis of all of the four limbs and the tail was evaluated by scoring in 4 ranks of scores of 0 to 3 and in 3 ranks of scores of 0 to 2, respectively, and the sum of the scores was determined as EAE score (the maximum score 14).

Incidence rates (the number of mice having developed the disease/the number of used mice) and the average of EAE score of each group were measured at the period of initial onset (on the 15th day after the immunization) and at the period of relapse (on the 38th day after the immunization). The results are shown in Table 4.

TABLE 4

| Test group | Number of animals | Period of initial onset | | Period of relapse | |
|---|---|---|---|---|---|
| | | Incidence rate | EAE score | Incidence rate | EAE score |
| Normal group | 2 | 0/2 | 0.0 | 0/2 | 0.0 |
| Control group | 8 | 6/8 | 6.8 | 6/8 | 1.9 |
| Compound A group | 8 | 1/8 | 1.4 | 2/8 | 0.3 |
| SASP group | 8 | 7/7 (1 animal died) | 5.5 | 6/6 (2 animals died) | 2.0 |

In the Compound A group, the incidence rate was low both at the period of initial onset and at the period of relapse, and the EAE score was obviously low too.

On the other hand, in the SASP group, neither the incidence rate nor the EAE score was lowered.

The above-described results reveal that Compound A suppressed the occurrence of paralysis of the chronic relapsing EAE. The effects of Compound A are obviously different from that of SASP, even though both of these drugs were categorized into immunomodulator.

The above-described results reveal that the compound of general formula [1] or the salt thereof is useful as an MIF inhibitor, and is also useful for a therapeutic or preventive treatment of a disease for which the inhibition of MIF is effective, such as NP and a relapse period of the relapsing-remitting and secondary progressive MS.

BRIEF DESCRIPTION OF DRAWING

FIG. 1 is a photograph of a membrane on which reactants resulting from binding between MIF and the antibody are detected by chemiluminescence.

INDUSTRIAL APPLICABILITY

A benzopyran derivative represented by general formula [1] or a salt thereof binds to MIF, exhibits an MIF inhibitory effect, and is useful for a therapeutic or preventive treatment of a disease for which the inhibition of MIF is effective.

The invention claimed is:

1. A method for treating the relapsing-remitting or secondary progressive multiple sclerosis at the time of relapse, comprising administering, to a subject in need thereof, a benzopyran derivative of formula (3) or a salt thereof:

[Formula 3]

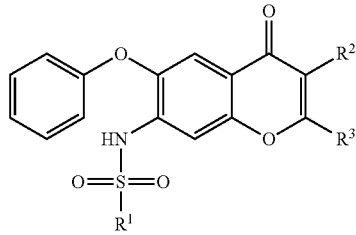

wherein
$R^1$ represents an optionally substituted $C_{1-6}$ alkyl group; one of $R^2$ and $R^3$ represents a hydrogen atom; and
the other of $R^2$ and $R^3$ represents a hydrogen atom, an optionally substituted amino group, an optionally substituted acylamino group, an optionally substituted carbamoyl group or an optionally substituted aryl group.

2. The method according to claim 1, wherein one of $R^2$ and $R^3$ represents a hydrogen atom; and the other of $R^2$ and $R^3$ represents an optionally substituted acylamino group.

3. The method according to claim 1, wherein the benzopyran derivative is N-[7-[(methylsulfonyl)amino]-4-oxo-6-phenoxy-4H-1-benzopyran-3-yl]formamide, N-(3-amino-4-oxo-6-phenoxy-4H-1-benzopyran-7-yl) methanesulfonamide, N-[7-[(methyl sulfonyl)amino]-4-oxo-6-phenoxy-4H-1-benzopyran-3-yl]acetamide, N-(4-oxo-6-phenoxy-4H-1-benzopyran-7-yl) methanesulfonamide, 7-[(methylsulfonyl)amino]-4-oxo-6-phenoxy-4H-1-benzopyran-2-carboxamide, N-[7-[(methylsulfonyl)amino]-4-oxo-6-phenoxy-4H-1-benzopyran-2-yl]acetamide, 7-[(methyl sulfonyl)amino]-4-oxo-6-phenoxy-4H-1-benzopyran-3-carboxamide, N-[7-[(ethylsulfonyl)amino]-4-oxo-6-phenoxy-4H-1-benzopyran-3-yl]formamide or N-(4-oxo-6-phenoxy-2-phenyl-4H-1-benzopyran-7-yl)methanesulfonamide.

4. The method according to claim 1, wherein the benzopyran derivative is N-[7-[(methylsulfonyl)amino]-4-oxo-6-phenoxy-4H-1-benzopyran-3-yl]formamide.

5. The method according to claim 1, wherein the method is for treating relapsing-remitting multiple sclerosis.

6. The method according to claim 1, wherein the method is for treating secondary progressive multiple sclerosis.

* * * * *